United States Patent
Hossack et al.

(10) Patent No.: US 7,750,537 B2
(45) Date of Patent: Jul. 6, 2010

(54) HYBRID DUAL LAYER DIAGNOSTIC ULTRASOUND TRANSDUCER ARRAY

(75) Inventors: John A. Hossack, Charlottesville, VA (US); Travis N. Blalock, Charlottesville, VA (US); William F. Walker, Earlysville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 492 days.

(21) Appl. No.: 11/840,079

(22) Filed: Aug. 16, 2007

(65) Prior Publication Data

US 2009/0048519 A1    Feb. 19, 2009

(51) Int. Cl.
*H01L 41/08* (2006.01)
(52) U.S. Cl. ........................ 310/334; 600/459
(58) Field of Classification Search ........ 310/334–337
See application file for complete search history.

(56) References Cited

U.S. PATENT DOCUMENTS

| | | | | |
|---|---|---|---|---|
| 5,792,058 | A | * | 8/1998 | Lee et al. .................... 600/459 |
| 5,825,117 | A | * | 10/1998 | Ossmann et al. ............ 310/317 |
| 5,920,972 | A | | 7/1999 | Palczewska et al. |
| 5,957,851 | A | * | 9/1999 | Hossack ...................... 600/459 |
| 6,416,478 | B1 | * | 7/2002 | Hossack ...................... 600/459 |
| 6,467,140 | B2 | * | 10/2002 | Gururaja .................... 29/25.35 |
| 6,514,618 | B1 | | 2/2003 | McKeighen |
| 6,656,124 | B2 | | 12/2003 | Flesch et al. |
| 7,527,592 | B2 | * | 5/2009 | Haugen et al. .............. 600/447 |

* cited by examiner

*Primary Examiner*—Mark Budd
(74) *Attorney, Agent, or Firm*—McDonnell Bohenen Hulbert & Berghoff LLP

(57) ABSTRACT

An ultrasound transducer array having a transmit transducer element comprising a transmit transducer material interposed between a transmit electrode and a reference electrode, wherein voltages applied across the transmit electrode and reference electrode induce an acoustic wave to emanate from the transmit transducer material; and a plurality of receive transducer elements positioned in an array on the transmit transducer element, each of the plurality of the receive transducer elements comprising a receive electrode and a receive transducer material interposed between the receive electrode and the reference electrode, and wherein acoustic waves applied to the plurality of receive transducer elements induces receive voltage signals on the receive electrodes with respect to the reference electrode.

20 Claims, 5 Drawing Sheets

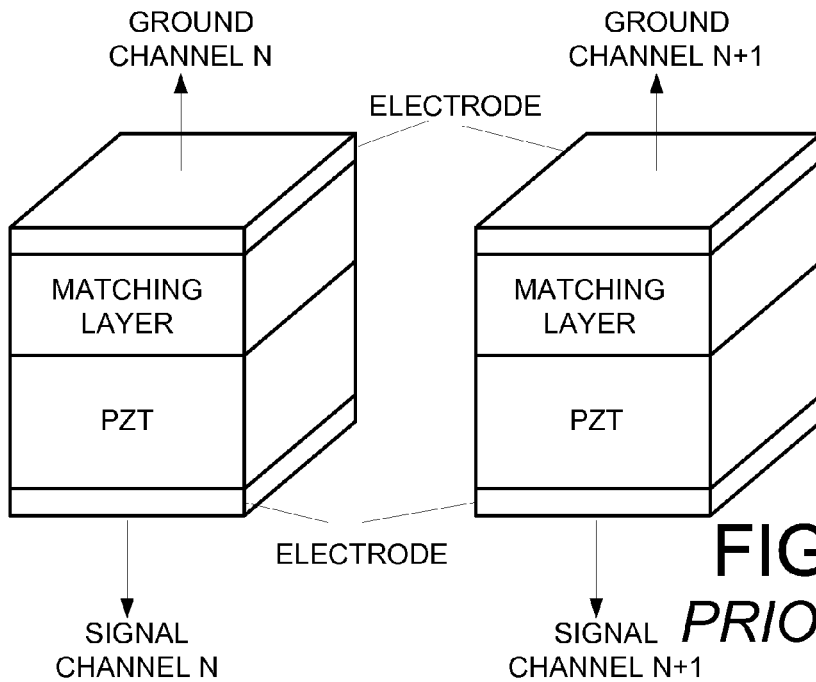
FIG. 1A *PRIOR ART*
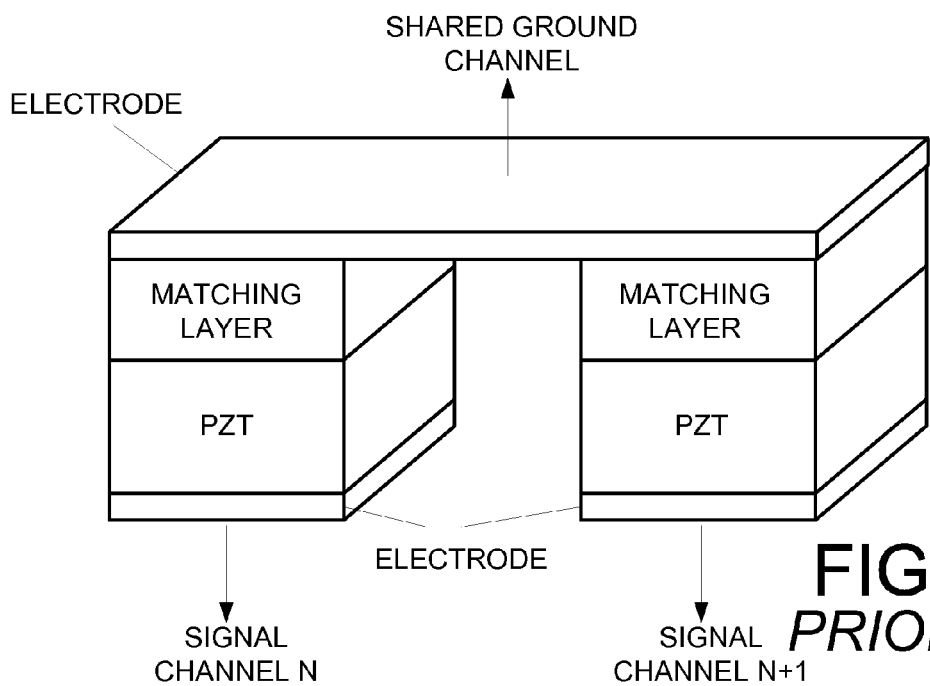
FIG. 1B *PRIOR ART*

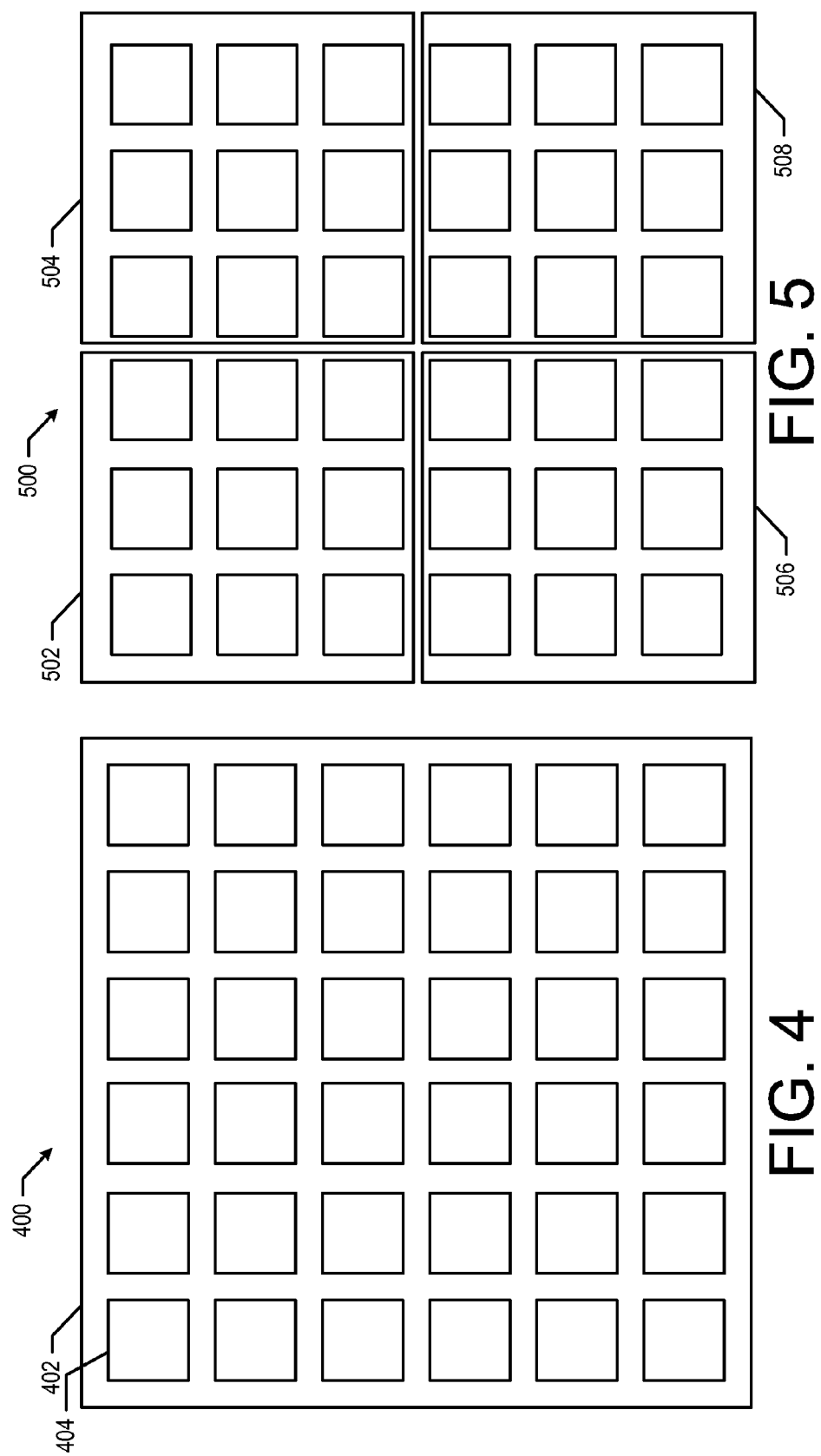

HYBRID DUAL LAYER DIAGNOSTIC ULTRASOUND TRANSDUCER ARRAY

STATEMENT AS TO RIGHTS TO INVENTIONS MADE UNDER FEDERALLY SPONSORED RESEARCH AND DEVELOPMENT

This invention was made with government support under grant no. NIH EB002349. The Government has certain rights in the invention.

FIELD

The present invention relates generally to diagnostic ultrasonic transducers.

BACKGROUND

Ultrasound imaging relies on the transmission and reception of acoustic waves. These acoustic waves are transduced from and to electrical analogous signals using electro-acoustic transducers. In diagnostic imaging, an array of closely spaced transducer elements is used. Frequently, the spacing of the elements is approximately one half or one whole wavelength according to whether or not beam steering is being used. In any event, transducer elements are tightly packed making fabrication difficult.

Ultrasound diagnostic imaging is a preferred modality for many radiology and cardiology applications. It is portable, non-invasive, involves no radiation, and can be made for relatively low cost. However, the vast majority of current ultrasound imaging systems today form 2D cross-sectional views (referred to as "B-Scans"—a 2D image plane perpendicular to the skin/transducer surface). In several applications, the B-Scan is not the preferred image format. In fact, for some applications it is preferable to use a "C-Scan"—a 2D image plane parallel to the skin/transducer surface. It is generally necessary to use a 2D transducer array and associated 2D matrix of processing channels to form a C-Scan image in real-time. Thus, the cost and complexity of the transducer array, array element signal connections and per-channel electronics and signal processing circuitry are also significant concerns.

One solution to the cost and complexity problem involves using a single common driver circuit to drive all $N^2$ channels (where N is the number of channels along each of the two dimensions of the array) for the transmit mode of operation and using discrete channel processing only in the receive mode of operation. This approach is particularly attractive since it can be configured to reduce the number of high voltage (and therefore large, costly and bulky) processing channels to one.

It is also preferable to use as low-cost electronic circuitry as possible—typically commercial CMOS. However, commercial CMOS circuitry is designed for low voltage operation and is easily damaged by high voltages similar to those frequently used for the transmit operation (30V-150V).

Therefore, in the typical ultrasonic transducer configuration, isolation must be provided between the transmit and receive circuitry to protect the receive circuitry from the high voltages used during transmit. In systems using a shared transmit driver, the low voltage connections (i.e., receive signal paths) may be temporarily connected to ground thus protecting the channels from high potentials, while the other side of the array that is normally the shared ground during receive is pulsed with a high voltage to generate a plane wave output from all transducer elements. This type of isolation has typically been provided through the use of multiplexer switches to ground or even disconnect the receive circuitry from the transducer elements during transmission.

In some prior art systems the isolation of the transmit and receive circuits is provided by shunt circuitry. That is, during the transmission of a pulse, the receive side of the transducer may be effectively grounded using shunt circuitry, such as diodes acting as a signal clamp to divert excess signal voltages caused by the signal transmission. During the receive operation, the transmit side of the electrode is grounded to provide a receive signal reference.

FIG. 1(A) shows a prior art transducer array. Only two elements are shown for clarity. In the case of a 2D array there may be 32-64 elements along each of two dimensions. The elements in FIG. 1A are show in isolation. In addition to the elements as shown, a common backing medium is located on the bottom surface of each element. The top surface of each transducer has a protective layer (e.g. RTV silicone or polyurethane) between the transducer and the load media (i.e. patient tissue under examination.) Notice that there is one active layer (PZT) in each transducer element, while the other layer is present to provide acoustic coupling. In the case of FIG. 1A, separate ground connections are made to all PZT elements. Practically speaking, these ground connections are connected together either at the array or at some other location.

FIG. 1B is a slightly modified version of FIG. 1A. In this case, a shared ground electrode covers all the top surface of all elements. Again, note that there is only one active layer (PZT) in each transducer element, while the other layer is present to provide acoustic coupling.

The transducers of FIGS. 1A and 1B use the same transducer elements for both transmit and receive, and thus each element has two electrodes. One disadvantage of the prior art arrays is that it is not practical to simultaneously optimally match the electrical impedance of the transmit and receive circuitry in this configuration. Specifically, all the transducer channels are operated electrically in parallel in the transmit mode but in an individual electrically isolated manner in the receive mode. Because the difference in transducer electrical impedance between transmit and receive is $N^2$ (e.g. 1024 or 4096), the electrical matching in both transmit and receive becomes extremely problematic. Imperfect transducer matching results in wasted electrical potential drops in the transmit/receive circuitry and this results in overall reduction in signal to noise ratio (SNR) and hence reduces either potential imaging penetration and/or imaging resolution (since a lower frequency may be required to mitigate signal attenuation/loss).

The transducers of FIG. 1C are multi-layered devices. One disadvantage of these types of transducers is that they require a large number of interconnections to the individual elements.

Thus, an improved transducer array is provided that overcomes some of the disadvantages of the prior, and provides additional benefits, as described herein.

SUMMARY

In a transducer array, separate electrical signal connections are applied to individual elements assigned to the receive operation. A common electrical signal connection is applied to an element (or elements operated electrically in parallel) for the transmit mode of operation. In this way, transmit and receive circuitry and transducer design can be optimized independently.

One preferred embodiment of an ultrasound transducer array comprises a transmit transducer element comprising a transmit transducer material interposed between a transmit electrode and a reference electrode, wherein voltages applied across the transmit electrode and reference electrode induce an acoustic wave to emanate from the transmit transducer material; and a plurality of receive transducer elements positioned in an array on the transmit transducer element, each of the plurality of the receive transducer elements comprising a receive electrode and a receive transducer material interposed between the receive electrode and the reference electrode, and wherein acoustic waves applied to the plurality of receive transducer elements induces receive voltage signals on the receive electrodes with respect to the reference electrode.

The ultrasound transducer materials are preferably acoustically matched relative to a load medium to reduce acoustic reflections. Preferably the acoustic impedance of the transmit transducer material has a value less than the acoustic impedance of the receive transducer material and greater than the acoustic impedance of a load medium, or greater than approximately 2 MRayls. Alternatively, the transmit transducer material has a value greater than 6-7 MRayls.

The transmit transducer material and the receive transducer material may comprise one or more of a piezoceramic layer, a piezo-polymer layer, a combination of piezoceramic and piezo-polymer layers, and electrostatic transducer material.

The arrays may have numerous layouts of the transmit and receive elements. In some embodiments, the array of receive elements is a one dimensional array, while a two-dimensional array is used in other embodiments.

In an alternative embodiment, the ultrasound transducer array comprises a plurality of transmit transducer elements, each comprising a transmit transducer material interposed between a transmit electrode and a reference electrode, wherein each of the transmit transducer elements is independently driven by a transmit signal; and, a plurality of receive transducer elements positioned in an array on each of the transmit transducer elements, each of the plurality of the receive transducer elements comprising a receive electrode and a receive transducer material interposed between the receive electrode and the reference electrode.

The transmit transducer elements may be rectangular or circular in shape. In some embodiments, the transmit transducers have a single row of receive transducer elements positioned thereon. Further, the transmit transducers may be rectangular, and positioned adjacent to each other, and each has a single row of receive elements. Alternatively, each transmit transducer may have a two-dimensional array of receive transducer elements. For instance, the transmit transducers may define quadrants of a rectangular region.

In yet another alternative embodiment, the ultrasound transducer array comprises a plurality of adjacent transmit transducers, each having a planar transmit transducer material interposed between a planar transmit electrode and a planar reference electrode; and each of the plurality of transmit transducers having a plurality of receive transducer elements positioned in an array on the respective planar transmit transducer, each of the plurality of receive transducer elements comprising a receive transducer material coupled to the respective planar reference electrode, a receive electrode coupled to the receive transducer material; and, wherein each of the plurality of adjacent transmit transducers are electrically isolated from each of the others of the plurality of transmit transducers, and each of the plurality of receive transducer elements is electrically isolated from each of the others of the plurality of receive transducers.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

BRIEF DESCRIPTION OF THE DRAWINGS

Presently preferred first and second embodiments are described below in conjunction with the appended drawing figures, wherein like reference numerals refer to like elements in the various figures, and wherein:

FIGS. 1A, 1B and 1C illustrate prior art transducers;

FIG. 4 illustrates an alternative embodiment of a transducer array;

FIG. 5 illustrates an alternative embodiment of a transducer array; and,

DETAILED DESCRIPTION

Figure 1C:
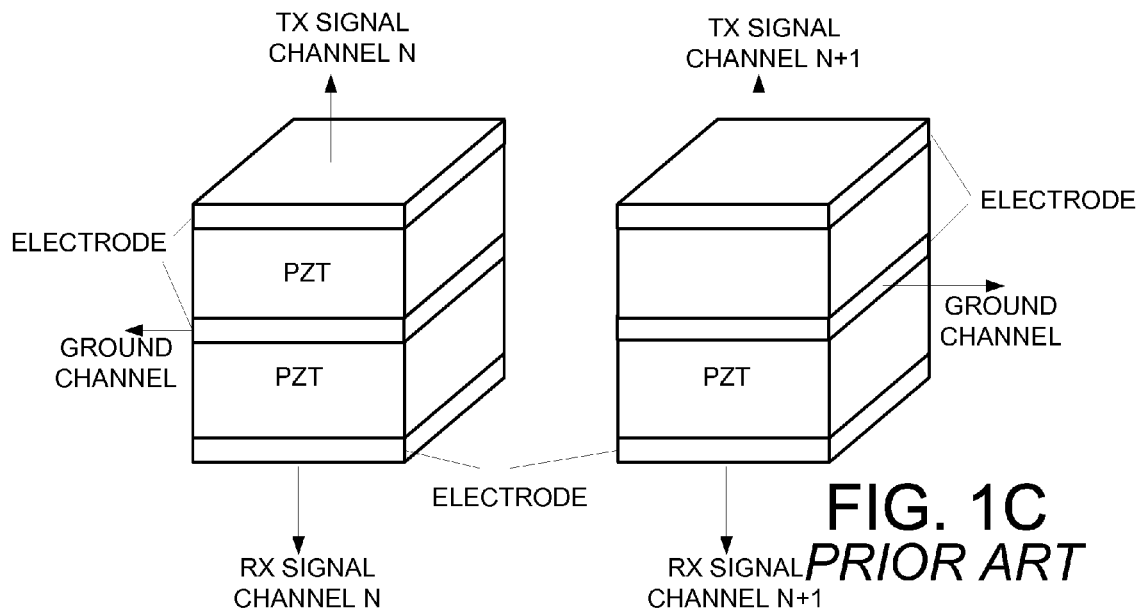
Figure 2:
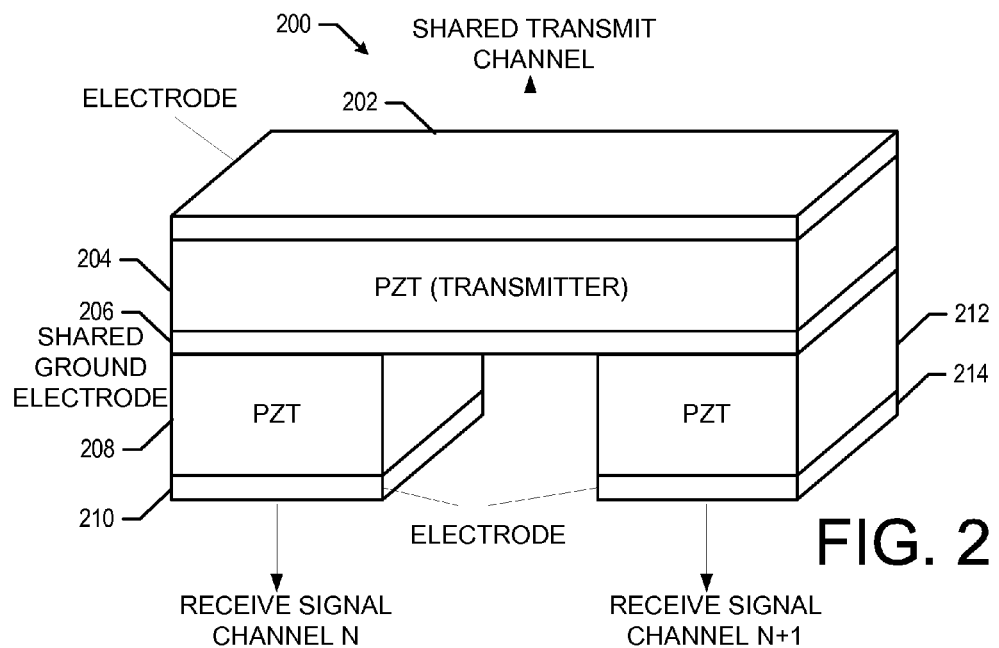
FIG. 2 illustrates one embodiment of a transducer array.

FIG. 2 illustrates a simplified block diagram of a preferred transducer system 200 having one transmit transducer and multiple receive transducers substantially coincident with the transmit transducer. This configuration is generally referred to herein as a transmit transducer having an array of receive transducers positioned thereon. The transmit transducer comprises electrode 202 and shared electrode 206, with transducer material 204 interposed between the electrodes 202, 206. The receive transducers comprise receive transducer material 208 and 212 interposed between the shared electrode 206 and the receive electrodes 210, 214, respectively. The transmit transducer operates when a transmit amplifier provides an electrical signal (a current or voltage) across the electrodes 202, 206, thereby causing ultrasonic emissions from the transducer. The receive elements each have separate electrical electrodes 210, 214 for the signal channels, but share the reference electrode 206 with the transmit transducer. The transducer array shown in FIG. 2 may be configured so that the load medium is positioned on either the top or bottom, as described more fully below.

Array Configurations

The array of receive transducers may be arranged in numerous configurations on the transmit transducer. For instance, the receive transducers may form a one dimensional or two dimensional array on a single transmit transducer. Two-dimensional arrays may be more useful in C-mode scanning applications, where the desired image is a planar area parallel to the transducer surface.

Figure 3:
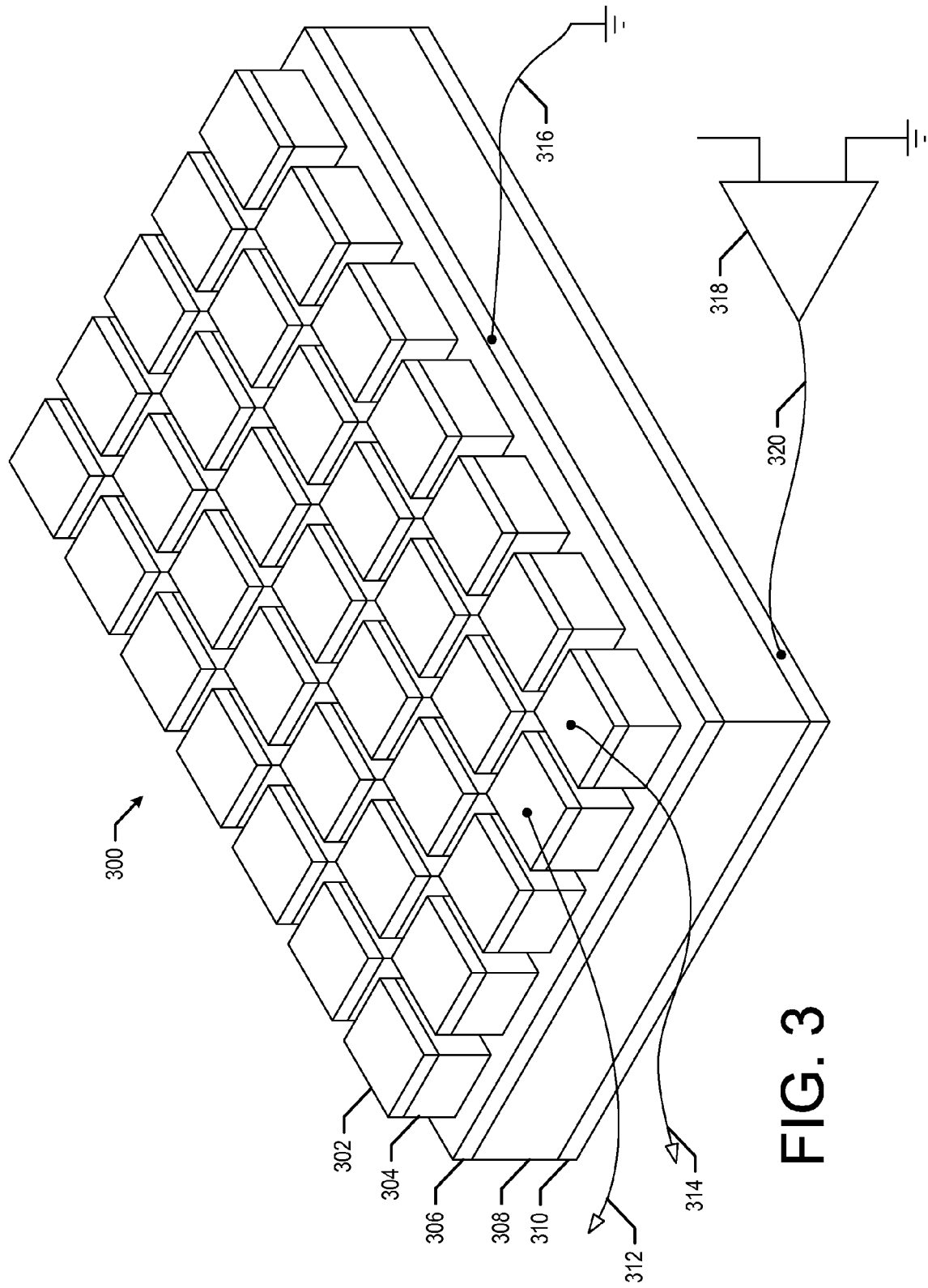
FIG. 3 illustrates an alternative embodiment of a transducer array.

FIG. 3 shows a single transmit transducer comprising transmit transducer material 308 interposed between the transmit electrode 310 and shared reference electrode 306. The transmit transducer is electrically driven by amplifier 318 connected to the transmit electrode 310 by conductor 320 and the shared reference electrode 306 by conductor 316. Substantially coincident with the transmit transducer is a 4×7 array of twenty-eight receive transducer elements such as the receive transducer element comprising receive transducer material 304 interposed between receive electrode 302 and shared electrode 306. Two other receive elements are shown connected to receive lines 312 and 314. The receive lines to the remaining receive elements are omitted for clarity of the drawing, but it is understood that each of the receive elements is connected to an electrical conductor, which is in turn connected to a receive channel signal processing circuit.

The receive elements shown in FIG. 3 are arranged in a rectangular row and column format, but other configurations are possible, including curvilinear arrangements. As one example, the receive elements may be configured as a single row along the transmit transducer. As a further alternative embodiment, the receive elements may form a curved array, either as a single curved or arcuate row, multiple curved or arcuate rows, or one or more circular or semicircular rows, The transmit transducer may also form one or more annular regions, or portions thereof, with receive transducers positioned along the curved transmit transducer.

FIG. 4 depicts a transducer 400 having a rectangular transmit region 402 with a 6×6 array of receive transducer elements including receive transducer element 404. However, the transmit transducer with the array of receive transducers may be arranged in numerous combinational configurations to obtain additional arrays as may be desired by the particular application. As an example, FIG. 5 depicts a transducer 500 having four transmit regions 502, 504, 506 and 508. Each transmit region has an associated 3×3 receive element array. Thus, the transducer face is divided into 4 quadrants, or 16 subapertures, and each of these is assigned an electrically isolated transmitter circuit. Using this approach, an approximate form of aperture selection and/or beam steering and focusing may be possible. Problems relating to undersampling will be partially mitigated by the finer sampling in the receive mode of operation.

Figure 6:
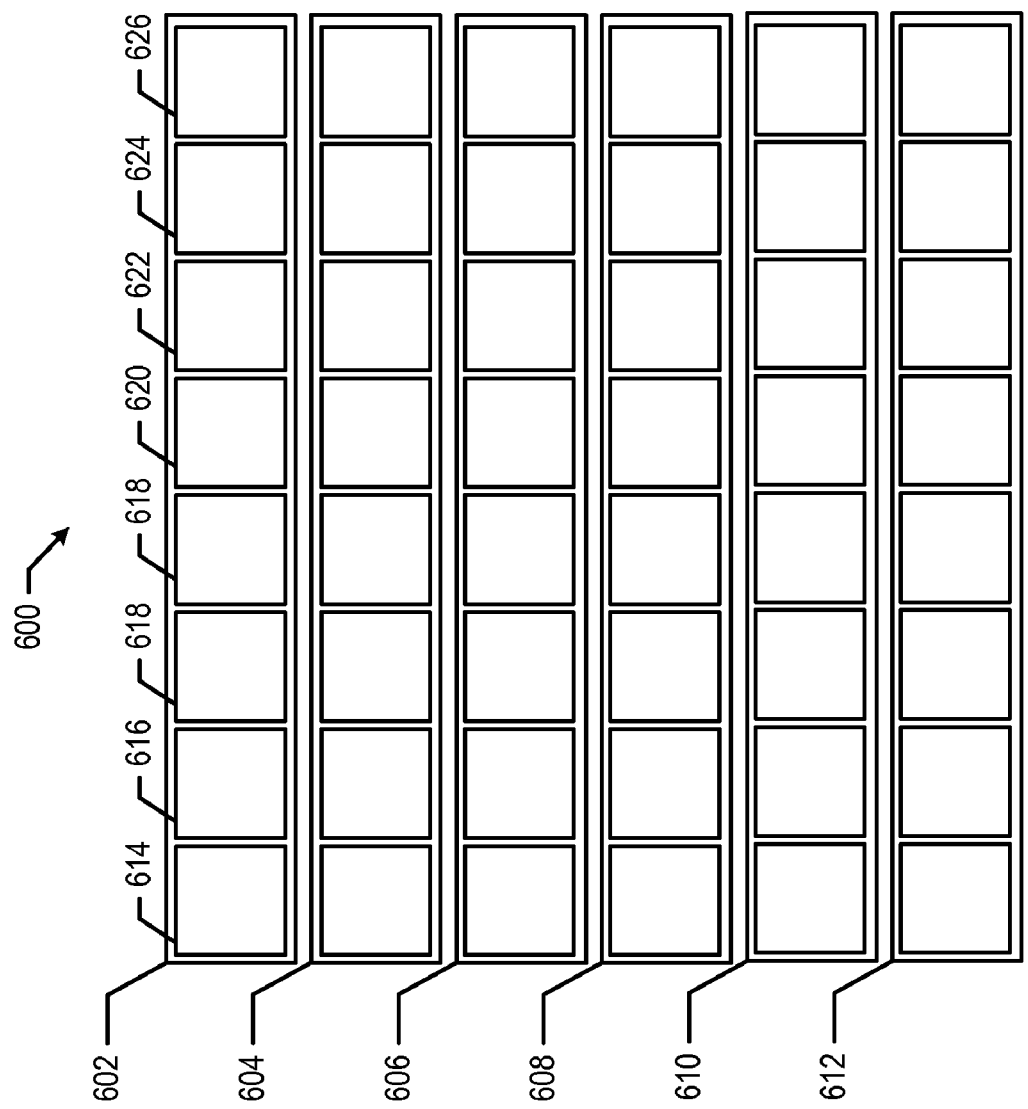
FIG. 6 illustrates an alternative embodiment of a transducer array.

As a further example, FIG. 6 depicts a transducer 600 that includes six transmit regions 602, 604, 606, 608, 610, and 612. Each transmit region has an associated array of multiple receive transducers substantially coincident with the transmit transducer. In particular, each such array is a one dimensional array, which for transmit transducer 602, comprises receive transducer elements 614, 616, 618, 620, 622, 624, and 626.

There are numerous other embodiments, which, for example, may include concentric annular transmit regions, each having a plurality of receive transducer element regions. In general, the embodiments all have at least one transmit region having more than one receive transducer element. In addition, while preferred, it is not required that each and every transmit transducer has more than one receive element, as long as at least one transmit transducer has more than one receive transducer.

In the simplest configuration, a common ground electrode is used at the interface between the transmitter transducer and the receiver transducers. However, electrically isolated connections can also be used. For example, separate ground conductors may be used for each of the transmit and receive transducer elements. In this case, the conducting layers would be isolated by an intervening non conducting material such as a polymer file (e.g., Kapton™).

In one embodiment, the configuration of the array is a 2D array of approximately 1024 or 4096 elements. However, it can also have different numbers in each dimensions (i.e. M×N elements) and this includes 1D, 1.25D, 1.5D, 1.75D (using the nomenclature described by GE ultrasound researchers in U.S. Pat. No. 5,897,501 (However, note that 1.5, 1.5 1.75 D are all subsets of a common definition of 2D array—i.e. they more precisely defined refinements) The arrays may be curved in either or both dimension and may include a focusing lens or a non-refractive "window".

Transducer Materials

Because the transducers are largely coincident, but their electrical termination conditions are very different (i.e. parallel connections or isolated connections), It is desirable to use transducer material with different electrical impedance properties for the transmit and receive transducers. The transducer materials may be combinations of: PZT (and other single phase piezoceramic materials), Piezo-polymers (e.g. PVDF and related piezo-polymer derivatives), piezoceramic/polymer composites (generally 1:3 composite materials) and electrostatic transducer technology ("cMUTs").

In certain embodiments such as electrostatic transducers, the transducer material may also be the electrode material. That is, a vacuum or gas is typically interposed between the plates of the transducer, and gas does not deform as a direct result of the transmit voltage. Rather, the voltage applied to the plates causes a relative displacement of the transducer electrodes. The resulting mechanical motion of the plates then induces transmission of an ultrasonic sound wave.

Because the receive transducer array comprises isolated elements, it is desirable to lower the electrical impedance of these elements are much as possible so that they are more amenable to electrical matching. In practice, this typically means that a high permittivity, "soft" piezoelectric ceramic such as PZT-5H or preferably CTS Wireless HD3203 (CTS Wireless, Albuquerque, N.Mex.) is used. Other ceramics and electroacoustic materials may be used and include other piezoceramics (Lead Titanate, Lead Metaniobate), other piezoelectric materials (piezopolymers—PVDF and PVDF derivatives) and ceramic epoxy composite materials, and single crystal piezoelectric materials including PZN:PT (TRS Ceramics, State College, Pa.). These materials have exceptionally high electromechanical coupling coefficients, which provide higher sensitivity and higher bandwidth.

The second layer, the transmitter layer, is preferably made from a different material than the receive layer underlying it. In fact, the transmitter layer can be configured as an acoustical matching layer for the underlying receive layer. For example, if the receive layer comprises a piezoceramic, then the overlying transmit layer may be made from approximately a quarter wavelength thick layer of 1:3 piezoceramic-polymer composite with a ceramic volume fraction selected so that acoustic impedance of this second layer lies intermediate between that of the ceramic material and the load media, typically human tissue, which has acoustic properties similar to water.

Alternatively, the transmit layer is made from a piezopolymer (e.g. PVDF) which also possesses an intermediate acoustic impedance. However, the acoustic impedance of PVDF is significantly lower than optimal—approximately 2.5 MRayls—whereas an acoustic impedance of approximately 6-7 MRayls is preferred. Because PVDF is normally only available in very thin sheets, it may be desirable to laminate several sheets together (e.g. 3 sheets) and to connect these sheets electrically in parallel if it is desired to reduce the electrical impedance of the transmitter or electrically in series if it is desired to increase the electrical impedance.

Any other combinations of electroacoustic materials are possible with transducer array structures described herein. For example, either of the transmitter and receiver may be any of: any piezoelectric ceramic, any single crystal piezoelectric material, any "relaxor" material requiring a bias to operate them, any piezopolymer or piezoceramic/polymer composite. Additionally, capacitive based transducers may be used for either or both of the transmitter/receiver layer (such as the cMUTs as described in Zhuang, "Two-dimensional capacitive micromachined ultrasonic transducer (CMUT) arrays for a miniature integrated volumetric ultrasonic imaging system", *Proceedings of the SPIE*, Volume 5750, pp. 37-46 (2005)).

Furthermore, the order of the stacking of the transmitter and receiver transducer elements may be reversed. The top layer is preferably the transmitter and lower layer the receiver. However, this order can be inverted, in which case the acoustic matching properties are also reversed. That is, the acoustic impedance of the transmit layer lies between the acoustic impedance of the receive layer and the load medium.

Each of the transmitter and receiver layer may in itself be a stacked (multi active layer) element. These transmitter (or receiver) layers are most simply connected electrically in parallel but each layer may be operated independently or the layers can be connected electrically in series.

The transducers described herein may be used in various ways, including volume acquisition such volumetric scans using a 2-D array of A-lines occupying 3-D space, as well as C-Scan imaging; B-Scan using a 1D or 2D array using the common transmit; various imaging modes: Gray scale imaging, all Doppler modes (blood flow, tissue, PW, Color etc.), harmonic modes (tissue and contrast); and elasticity imaging using the common transmit region with special waveforms (typically long pulse duration—high duty cycle) to cause tissue displacement that can be tracked using separately operated short pulse (high resolution) operation.

A preferred embodiment of the present invention has been described above. Those skilled in the art will understand, however, that changes and modifications may be made to these embodiments, and that the arrangements and functions described herein are set forth for purposes of example only. As such, those skilled in the art will appreciate that other arrangements and other elements can be used instead, and elements can be added, omitted, combined, distributed, re-ordered, re-positioned, or modified in other ways.

We claim:

1. An ultrasound transducer array comprising:
    a transmit transducer element comprising a transmit transducer material interposed between a transmit electrode and a reference electrode, wherein voltages applied across the transmit electrode and reference electrode induce an acoustic wave to emanate from the transmit transducer material; and
    a plurality of receive transducer elements positioned in an array on the transmit transducer element, each of the plurality of the receive transducer elements comprising a receive electrode and a receive transducer material interposed between the receive electrode and the reference electrode, and wherein acoustic waves applied to the plurality of receive transducer elements induces receive voltage signals on the receive electrodes with respect to the reference electrode.

2. The ultrasound transducer of claim 1, wherein an acoustic impedance of the transmit transducer material has a value less than the acoustic impedance of the receive transducer material and greater than the acoustic impedance of a load medium.

3. The ultrasound transducer array of claim 1, wherein the acoustic impedance of the transmit transducer material is less than the acoustic impedance of the receive transducer material and greater than approximately 2 MRayls.

4. The ultrasound transducer array of claim 1, wherein at least one of the transmit transducer material and the receive transducer material comprise a piezoceramic layer.

5. The ultrasound transducer array of claim 1, wherein at least one of the transmit transducer material and the receive transducer material comprise a piezo-polymer layer.

6. The ultrasound transducer array of claim 1, wherein at least one of the transmit transducer material and the receive transducer material comprise a combination of piezoceramic and piezo-polymer layers.

7. The ultrasound transducer array of claim 1, wherein at least one of the transmit transducer material and the receive transducer material operate in an electrostatic mode.

8. The ultrasound transducer array of claim 1, wherein the array is a one dimensional array.

9. The ultrasound transducer array of claim 1 wherein the array is a two-dimensional array.

10. An ultrasound transducer array comprising:
    a plurality of transmit transducer elements, each comprising a transmit transducer material interposed between a transmit electrode and a reference electrode, wherein each of the transmit transducer elements is independently driven by a transmit signal; and,
    a plurality of receive transducer elements positioned in an array on each of the transmit transducer elements, each of the plurality of the receive transducer elements comprising a receive electrode and a receive transducer material interposed between the receive electrode and the reference electrode.

11. The ultrasound transducer array of claim 10, wherein at least some of the transmit transducer elements are rectangular.

12. The ultrasound transducer array of claim 10 wherein at least one of the plurality of transmit transducers has a single row of receive transducer elements positioned thereon.

13. The ultrasound transducer array of claim 10, wherein the transmit transducers are rectangular, and each has a single row of receive elements.

14. The ultrasound transducer array of claim 10 wherein each transmit transducer has a two-dimensional array of receive transducer elements.

15. An ultrasound transducer array comprising:
    a plurality of adjacent transmit transducers, each having a planar transmit transducer material interposed between a planar transmit electrode and a planar reference electrode; and
    each of the plurality of transmit transducers having a plurality of receive transducer elements positioned in an array on the respective planar transmit transducer, each of the plurality of receive transducer elements comprising a receive transducer material coupled to the respective planar reference electrode, a receive electrode coupled to the receive transducer material; and,
    wherein each of the plurality of adjacent transmit transducers are electrically isolated from each of the others of the plurality of transmit transducers, and each of the plurality of receive transducer elements is electrically isolated from each of the others of the plurality of receive transducers.

16. The ultrasound transducer array of claim 15, wherein the plurality of adjacent transmit transducers are each rectangular transducers and define quadrants of a larger rectangular region.

17. The ultrasound transducer array of claim 15, wherein the plurality of adjacent transmit transducers are each rectangular transducers and wherein each of the plurality of receive transducer elements positioned in an array comprises a one dimensional array.

18. The ultrasound transducer array of claim 17 wherein each of the plurality of receive transducer elements associated with each of the adjacent transmit regions define apertures.

19. The ultrasound transducer array of claim 15 wherein each of the plurality of receive transducer elements positioned in an array comprises a two-dimensional array.

20. The ultrasound transducer array of claim 15 wherein the transmit transducer material and receive transducer material are acoustically matched relative to a load medium to reduce acoustic reflections.

* * * * *